(12) United States Patent
ÀBrassard et al.

(10) Patent No.: US 9,108,191 B2
(45) Date of Patent: Aug. 18, 2015

(54) DEVICE AND METHOD FOR THE COMPLETE UPTAKE OF LIQUIDS FROM VESSELS

(75) Inventors: Lothar À Brassard, Heinsberg (DE); Uwe Jäntges, Aachen (DE)

(73) Assignee: PerkinElmer chemagen Technologie GmbH, Baesweiler (DE)

( * ) Notice: Subject to any disclaimer, the term of this patent is extended or adjusted under 35 U.S.C. 154(b) by 441 days.

(21) Appl. No.: 13/701,216

(22) PCT Filed: May 14, 2011

(86) PCT No.: PCT/EP2011/002396
§ 371 (c)(1),
(2), (4) Date: Nov. 30, 2012

(87) PCT Pub. No.: WO2011/151014
PCT Pub. Date: Dec. 8, 2011

(65) Prior Publication Data
US 2013/0068042 A1    Mar. 21, 2013

(30) Foreign Application Priority Data
Jun. 2, 2010 (DE) .......................... 10 2010 022 552

(51) Int. Cl.
*B01L 3/02* (2006.01)
*B01L 3/14* (2006.01)
(Continued)

(52) U.S. Cl.
CPC . *B01L 3/021* (2013.01); *B01L 3/02* (2013.01); *B01L 3/14* (2013.01); *B01L 9/06* (2013.01);
(Continued)

(58) Field of Classification Search
CPC ............. B01L 3/02; B01L 3/021; B01L 3/14; B01L 9/06; B01L 2200/0642; B01L 2200/146; B01L 2400/0478; G01N 35/1009; G01N 35/10
USPC ............... 73/863.01, 864.01, 864.73, 864.74; 422/524
See application file for complete search history.

(56) References Cited

U.S. PATENT DOCUMENTS 2,437,697 A * 3/1948 Kalom ......................... 600/550
3,991,627 A   11/1976 Laird et al.
(Continued)

FOREIGN PATENT DOCUMENTS

DE      2807262 A1    8/1978
DE     19756842 A1    5/1999
(Continued)

OTHER PUBLICATIONS

Office Action issued Dec. 8, 2010 in DE Application No. 10 2010 022 552.5, (in German with no reference codes).
(Continued)

*Primary Examiner* — Thomas P Noland
(74) *Attorney, Agent, or Firm* — Panitch Schwarze Belisario & Nadel LLP

(57) ABSTRACT

A device is provided for the complete uptake of liquids from vessels using removal units having removal tips. The removal tips or the vessel bottoms are configured or arranged relative to one another such that the area of the surface of a vessel bottom on which the respective removal tip would touch down, when that removal tip is inserted into the vessel, and the end surface of the removal tip are tilted relative to each another, at least on a portion of the two surfaces. That is to say, the surfaces are not parallel there.

15 Claims, 3 Drawing Sheets

(51) Int. Cl.
  *B01L 9/06* (2006.01)
  *G01N 35/10* (2006.01)

(52) U.S. Cl.
  CPC ..... *G01N 35/1009* (2013.01); *B01L 2200/0642* (2013.01); *B01L 2200/146* (2013.01); *B01L 2400/0478* (2013.01); *G01N 35/10* (2013.01)

(56) References Cited

U.S. PATENT DOCUMENTS

| | | | |
|---|---|---|---|
| 4,094,641 A | 6/1978 | Friswell | |
| 4,944,922 A | 7/1990 | Hayashi | |
| 5,129,539 A * | 7/1992 | Wakatake | 73/864.01 X |
| 5,895,630 A | 4/1999 | Skaborn et al. | |
| 6,143,250 A | 11/2000 | Tajima | |
| 6,146,881 A * | 11/2000 | Hering | 422/524 X |
| 6,148,666 A | 11/2000 | Roesicke | |
| 6,150,103 A * | 11/2000 | Ness et al. | B01L 3/02 |
| 6,270,726 B1 | 8/2001 | Tyberg et al. | |
| 6,363,802 B1 | 4/2002 | Grippo et al. | |
| 7,318,911 B2 * | 1/2008 | Smith | B01L 3/02 |
| 7,637,175 B1 | 12/2009 | Wiederin et al. | |
| 7,785,466 B1 * | 8/2010 | Smith | 422/524 X |
| 8,202,495 B1 * | 6/2012 | Smith | 422/524 |
| 8,997,800 B2 * | 4/2015 | Voit et al. | G01N 35/10 |
| 2001/0007643 A1 * | 7/2001 | Horner et al. | B01L 9/06 |
| 2005/0209531 A1 * | 9/2005 | Rising et al. | B01L 2200/0642 |
| 2007/0012123 A1 | 1/2007 | Li et al. | |
| 2007/0231217 A1 | 10/2007 | Clinton et al. | |
| 2008/0095665 A1 * | 4/2008 | Smith | B01L 3/02 |
| 2010/0273243 A1 | 10/2010 | Oue et al. | |
| 2011/0195518 A1 * | 8/2011 | Gjerde et al. | 422/524 X |

FOREIGN PATENT DOCUMENTS

| | | | |
|---|---|---|---|
| DE | 69914029 T2 | 11/2004 | |
| DE | 60031526 T2 | 6/2007 | |
| DE | 102006020286 A1 | 10/2007 | |
| DE | 102007004856 A1 | 8/2008 | |
| DE | 102008058065 A1 | 5/2010 | |
| EP | 0984285 B1 | 1/2004 | |
| EP | 1183104 B1 | 10/2006 | |
| EP | 1933154 A2 | 6/2008 | |
| GB | 2341804 A * | 3/2000 | A61M 5/32 |
| JP | 55-039029 A | 3/1980 | |
| JP | 2011058897 A * | 3/2011 | G01N 35/10 |
| JP | 2011058902 A * | 3/2011 | G01N 35/10 |
| WO | 2007124926 A1 | 11/2007 | |
| WO | 2008092607 A1 | 8/2008 | |
| WO | 2009084451 A1 | 7/2009 | |
| WO | 2010057861 A2 | 5/2010 | |

OTHER PUBLICATIONS

Int'l Search Report issued Aug. 26, 2011 in Int'l Application No. PCT/EP2011/002396.
Int'l Preliminary Report on Patentability issued Dec. 13, 2012 in Int'l Application No. PCT/EP2011/002396.
Written Opinion issued Aug. 26, 2011 in Int'l Application No. PCT/EP2011/002396, (in German).
Response to Written Opinion dated Dec. 8, 2011 in Int'l Application No. PCT/EP2011/002396, (in German).
Written Opinion issued May 21, 2012 in Int'l Application No. PCT/EP2011/002396, (in German ).
Response to Written Opinion dated Jun. 22, 2012 in Int'l Application No. PCT/EP2011/002396, (in German).

* cited by examiner

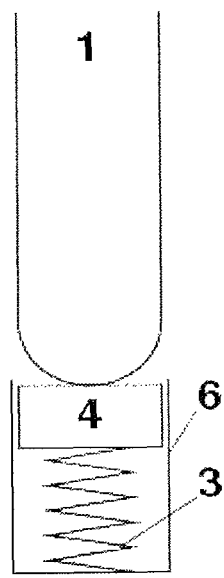
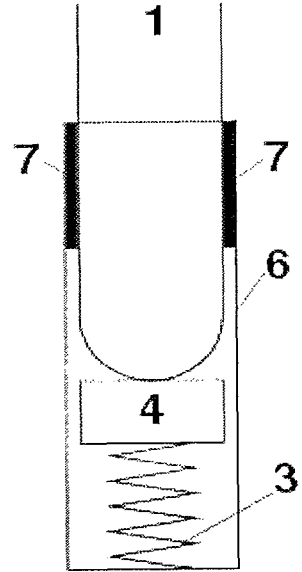
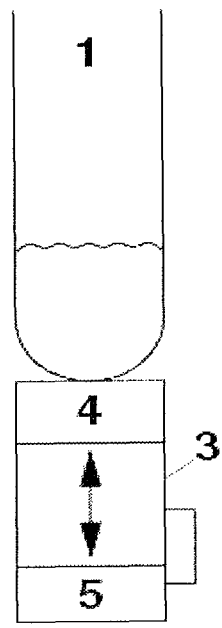
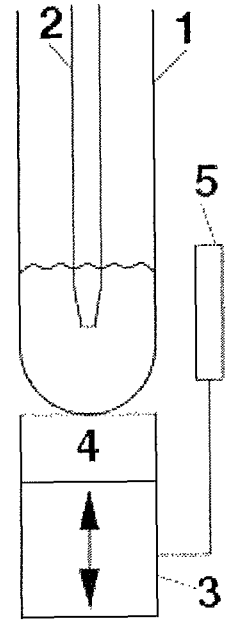

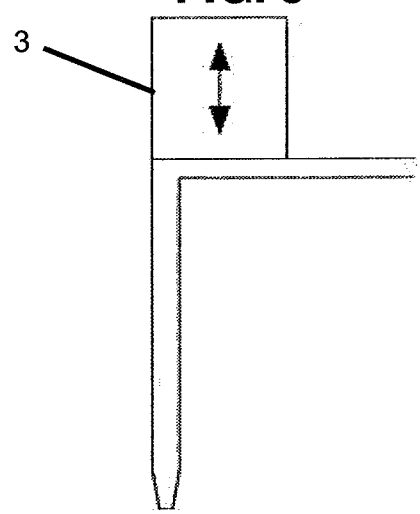
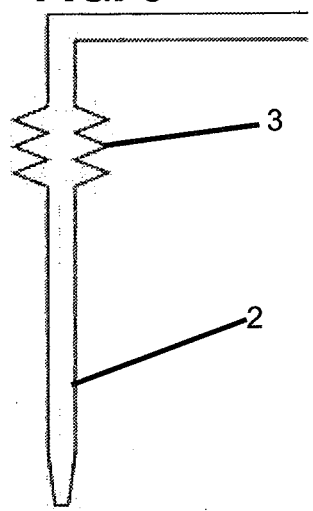
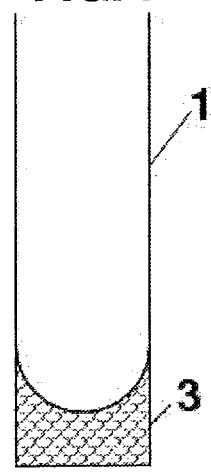

DEVICE AND METHOD FOR THE COMPLETE UPTAKE OF LIQUIDS FROM VESSELS

CROSS-REFERENCE TO RELATED APPLICATIONS

This application is a Section 371 of International Application No. PCT/EP2011/002396, filed May 14, 2011, which was published in the German language on Dec. 8, 2011, under International Publication No. WO 2011/151014 A1 and the disclosure of which is incorporated herein by reference.

BACKGROUND OF THE INVENTION

The present invention relates to a device and a method for the complete (i.e., remainder-less) uptake of liquids from vessels, more particularly, for removing reagents from reaction vessels using pipettes.

Especially with applications in the field of laboratory analysis, different processes are often combined. In such cases, special vessels are used, inter alia, for receiving liquids, these liquids being removed again in the course of the application.

Because of progressing automation, robotic systems (e.g. automated liquid handling systems) are being increasingly employed to transfer a sample extract from one vessel of a first process to a corresponding container for a second process, for example.

These systems for liquid transfer mostly include removal units (e.g. pipettes) that are lowered from above into the vessels, which are, as a rule, upright, and suck the liquid out of the vessels.

The removal units include a removal tip that is immersed in the liquid in order to remove the liquid. This tip is shaped such that a channel, through which the liquid is able to flow, is surrounded by a wall. The channel begins at the removal tip and extends through the removal unit.

When there is an underpressure in the channel, the liquid is sucked out of the vessel. In this way the liquid is removed.

The removal tip has an end surface at its end, which is defined by the confining wall.

A disadvantage of these existing systems for liquid transfer is that the liquid cannot be removed from the vessels with any, or at least almost no, liquid remaining therein. For this reason, it is currently not possible to remove, in particular, small amounts of liquid from the vessels, or this can be achieved only with great difficulty.

The reason for this is that there must always remain a certain residual volume in the vessel since, when attempting to quantitatively transfer the liquid, there is a risk of an airtight and liquid-tight seal forming between the removal tip of a removal unit and the vessel bottom, due to too low positioning of the removal unit. For example, a pipette tip, as a rule, must not touch the bottom of the vessel, since on drawing up the liquid, an underpressure is formed, which suctions the pipette tip to the vessel bottom, and uptake of liquid is initially impossible, as the liquid is not able to enter the pipette tip.

With the subsequent upward movement of the pipette tip, while the underpressure persists, the connection to the vessel bottom is released and the liquid shoots up into the tip in an uncontrolled manner. In the process, the liquid is in most cases sucked in up to the filter, which makes subsequent controlled dispensing impossible.

The existing problem is made worse by variances with respect to dimensioning and shape of the plastic materials (e.g. pipette tips, vessels). For high-sensitivity applications in the field of PCR-based analysis, an automated quantitative transfer of small volumes of liquid is necessary, since all previous measures lead to sensitivity losses or total loss.

BRIEF SUMMARY OF THE INVENTION

An object of the present invention was to provide a device and a method which overcome the above-mentioned disadvantages and which are suited for a complete uptake of liquids from vessels.

This object is achieved with a device for the complete uptake of liquids comprising a removal unit having a removal tip and a vessel containing the liquid to be removed, wherein the removal tip or the vessel bottom are configured or arranged relative to each other such that the area of the surface of the vessel bottom on which the removal tip would touch down, when the removal tip is inserted into the vessel, and the end surface of the removal tip are tilted relative to each other, at least in a portion of the two surface areas, that is to say the surfaces are not parallel there.

In this way, even if the removal tip touches down on the vessel bottom there will always result a gap between the corresponding area of the bottom and the end surface of the removal tip, so that the removal tip is prevented from suctioning to the bottom. In this case, the liquid is able to flow through the gap into the removal unit.

Preferred arrangements or shapes, either alone or in combination with one another, are:
  the bottom of the vessel is positioned so as to be oblique relative to the end surface of the removal tip;
  the bottom of the vessel is curved, the removal tip being arranged eccentrically to the apex of the curvature;
  the end surface of the removal tip is beveled relative to the longitudinal axis of the removal tip or has another shape that deviates from the planar surface as, for example, the shape of a crown, or slots are incorporated in the otherwise planar end surface.

If the vessel is curved at its bottom end, it is advantageous, for example, to position the vessel below the removal unit in such a way that the tip of the removal unit would touch the bottom of the vessel at a small distance, i.e. ⅕th - 1/100th of the vessel diameter, from the apex of the curvature.

One preferred embodiment comprises, in addition, at least one compensation element which is suited for ensuring that, if the removal tip touches the vessel bottom when the removal tip is being inserted into the vessel, the vessel or the removal tip can perform an evasive movement in the direction of the relative direction of movement of the removal tip and vessel.

This is the case, for example, if the vessel and/or the removal tip is resiliently supported.

Preferred compensation elements are active or passive elements or combinations of active and passive elements.

Preferred passive elements are springs or other resilient materials, such as resilient plastics, for example foamed plastics or rubber. Springs suitable for use are, in particular, spiral or leaf springs.

The passive elements are advantageous in that compensation of the pressure acting on the vessel bottom and the removal tip is accomplished easily and without additional control.

When the removal tip touches down on the vessel bottom, the latter automatically, by action of the elastic compensation element, performs an evasive downward movement, or the removal tip performs an evasive upward movement.

Preferred active elements are piezo elements, muscle wires or motors, which, preferably each fitted with mechanics, effect a compensation of the pressure when the removal tip touches the vessel bottom.

In one preferred embodiment, these active elements are provided with a sensor, which measures the contact pressure, and with control electronics controlling the deflection of the compensation element.

Active control of the pressure between the removal tip and the vessel bottom is advantageous in that failures, such as tilting, can be compensated.

In one preferred embodiment, the compensation elements are made of commercially available resilient material. A compensation element, in particular, comprises elastic plastics or springs.

In one preferred embodiment, the vessel is arranged on the compensation element, preferably in a vertical or slightly tilted position, the vessel preferably being retained by a holding device which is fitted on the compensation element.

The vessel may be connected to the compensation element or the holding device either detachably or non-detachably. A detachable connection has the advantage that the vessel can be readily replaced and that, for example, disposable vessels can be used.

Preferably, the vessel on the compensation element or on the holding device is merely placed thereon.

In the case of the first preferred embodiment, the compensation element is preferably mounted on a base plate to ensure that the element stands safely.

In a further preferred embodiment, the compensation element is arranged directly in or on the removal unit, so that the complete removal unit is elastically mounted, or a part of the wall of the removal unit is made of an elastic material or is configured as a bellows, so that at least the removal tip is elastically mounted.

In another preferred embodiment, compensation elements are arranged both on the vessel and on the removal unit.

To avoid tilting, the compensation element is preferably arranged in a guide unit as, for example, a sleeve which has at least one opening at its top side. This guide unit has guide elements that guide the compensation element, the holding device, the vessel, or the removal unit along a straight path. Preferably, the walls of the above-mentioned sleeve form the guide elements.

The length of the guide unit is such that it may receive the compensation element, preferably along with the holding device and, especially preferably, also receives at least part of the vessel or of the removal unit.

The removal unit is preferably fixedly attached to the base plate; in particular, the guide unit is screwed on the base plate with a thread.

In yet another preferred embodiment, the compensation element is configured as a distance adjustment element, which is suited for changing the relative vertical distance between the vessel bottom and the tip of the removal unit, as a function of the amount of liquid in the vessel when a liquid is being taken up from a vessel by a removal unit, in such a way that, as an increasing amount of liquid is removed, the distance between the vessel bottom and the tip of the removal unit decreases.

The tip of the removal unit should always remain below the level of the liquid during removal, to prevent air from being sucked in.

With a liquid-filled vessel into which a removal unit is being inserted, the removal process, in this case, is as follows:

In the filled state of the vessel, the distance between the vessel bottom and the tip of the removal unit is adjusted by the distance adjustment element so as to be at its maximum.

The removal unit removes liquid from the vessel. Because of this removal of liquid, the removal unit will become heavier, as a function of the amount of liquid, and the vessel will become lighter. In addition, the liquid level will rise in the removal unit, and it will drop in the vessel.

As the removal unit continues to remove liquid, this distance is continuously reduced by the distance adjustment element, as a function of the amount of liquid taken up. During this process, the tip of the removal unit should always lie below the liquid level in the vessel.

As a measure for the removed liquid, on the one hand, the weight force of the liquid that has been taken up or which has remained in the vessel may be used or, on the other hand, the liquid level in the vessel or in the removal unit may be used.

The tip of the removal unit should not touch the vessel bottom, or at least not before the liquid has been almost completely sucked up.

Preferred distance adjustment elements are active or passive elements, or combinations of active and passive elements.

Suitable passive elements regulate the distance between the vessel bottom and the tip of the removal unit, preferably via the weight force of the amount of liquid contained in the vessel.

With passive distance adjustment elements, regulation of the distance between the vessel bottom and the tip of the removal unit is automatically effected due to the always differing weight force of the amount of liquid transferred, if the distance adjustment element is arranged below the vessel or at the removal unit. The vessel becomes lighter and is automatically, by the elastic distance adjustment element, pressed upwards, or the removal unit becomes heavier and automatically advances downwards.

Suitable active elements preferably regulate the distance between the vessel bottom and the tip of the removal unit via the weight force of the amount of liquid contained in the vessel or taken up by the removal unit, or via the liquid level thereof.

In a preferred embodiment, these elements are fitted with a sensor measuring the amount of liquid, and with control electronics controlling the deflection of the distance adjustment element.

Active distance adjustment has the advantage that failures, such as tilting, can be compensated. If the height of the liquid level in the vessel is measured by the sensor, this has the additional advantage that it is possible to simultaneously monitor whether the tip of the removal unit is in fact always below the liquid level.

Preferably, passive distance adjustment elements for non-homogeneously formed (e.g. curved at the end) vessels are configured such that the vessel is lifted in such a way that, as the amount of liquid declines, the change in distance becomes continuously smaller per unit of liquid removed.

Particularly with resilient embodiments it is advantageous if the spring forces effective at the end of the process are weaker. This is achieved by providing an arrangement of springs of differing strength, or one spring with non-homogeneous deflection per weight force.

The device can be designed for one or more reaction vessels or removal units, for simultaneous or successive removal. In an advantageous embodiment, each sample vessel, or each removal unit, is individually supported in order to compensate any variances. The device is preferably adapted for reaction plates in the 12-, 24- or 96-well formats, by grid-like arrangement of a corresponding number of the devices.

The device is preferably dimensioned such that it can be used with commercially available automated devices (liquid handlers) or in manual operations using pipettes.

The device preferably includes calibration elements for calibrating the distance between the removal unit and the vessel bottom, preferably in a clearly defined state of the device.

In one preferred embodiment, the compensation element is integrated directly in the vessel bottom, in particular, the vessel bottom consists of a resilient material; the vessel bottom may, for example, be foamed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIGS. 3A and 3B are schematic representations showing embodiments of the device according to the invention having holders based on springs;

FIGS. 4A and 4B are schematic representations showing embodiments of the device according to the invention having active compensation elements;

FIG. 5 is a schematic representation showing an embodiment of a device according to the invention having a compensation element on the removal unit;

FIG. 6 is a schematic representation showing an embodiment of the device according to the invention having a compensation element integrated in the removal unit; and FIG. 7 is a schematic representation showing an embodiment of a vessel according to the invention having an integrated compensation element.

DETAILED DESCRIPTION OF THE INVENTION

Figure 1:
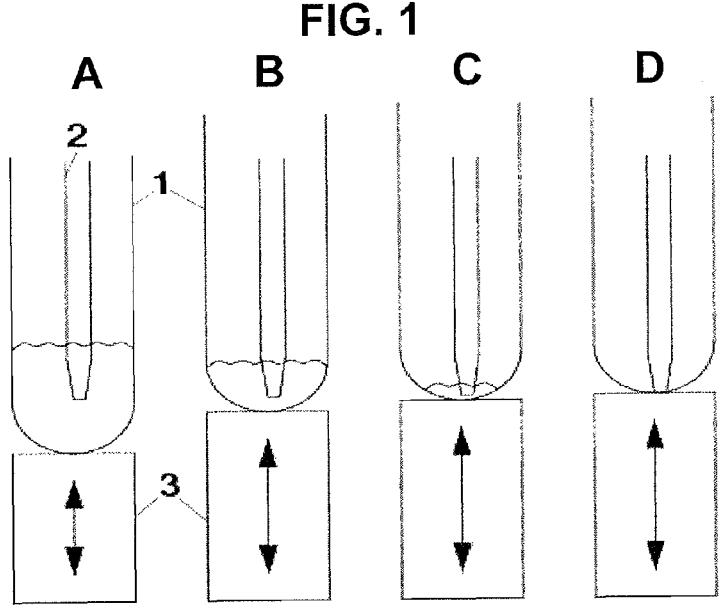
FIG. 1 is a schematic representation of the constitution of the device and of the sequence of the method according to the invention, shown in parts A to D.

In FIG. 1, part A, a compensation element 3 is shown, on which is arranged a vessel 1 filled with a liquid. A pipette 2 has been inserted in the vessel to remove liquid.

In the example, the pipette is arranged in a position slightly eccentric to the apex of the vessel bottom to prevent the pipette tip from suctioning to the bottom.

In FIG. 1, parts B and C, the compensation element simultaneously acts as a distance adjustment element. When liquid is removed from the vessel by the pipette (part B), the liquid level in the vessel and the weight force exerted by the liquid on the distance adjustment element drop. The vessel is thereby becoming lighter, is pushed upwards by the distance adjustment element.

The vessel is pushed up (part C) until the tip of the pipette touches down on the bottom of the vessel or, at least, is located at a very close distance above the bottom (part D).

In FIG. 1, part D, the compensation element acts such that the pressure exerted on the vessel bottom by the pipette tip upon contacting the bottom, is compensated by the vessel performing a slight evasive downward movement.

Figure 2A:
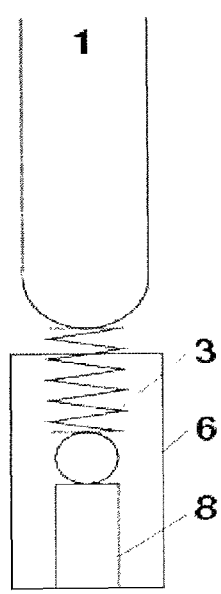
FIGS. 2A and 2B are schematic representations showing embodiments of the device according to the invention, based on springs.

In FIG. 2A the vessel 1 is placed directly on a spring or a resilient plastic as compensation element 3, the compensation element being arranged inside a sleeve 6, on a mounting unit 8.

Figure 2B:
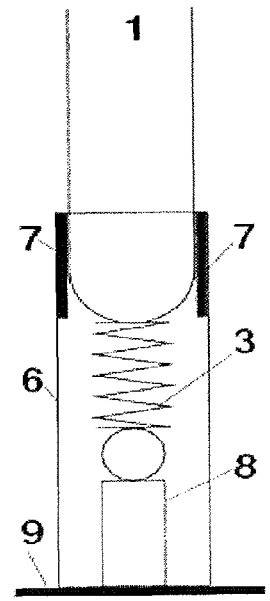

In FIG. 2B the sleeve 6 is of a length sufficient for the vessel to be guided safely and along a straight path by guide elements 7. In addition, the sleeve and the mounting unit are arranged on a base plate 9.

FIGS. 3A and 3B correspond to the construction in FIGS. 2A and 2B, except that the compensation element is borne directly on the bottom of the sleeve and that the device is held by a holding device 4.

In FIGS. 4A and 4B the vessel is held by a holding device 4 which is connected to an active compensation element. The compensation element is controlled by a sensor having a control unit 5. This element 5 measures, in FIG. 4A, the weight force of the vessel and, in FIG. 4B, the height of the liquid level, while here simultaneously measuring the immersion depth of the pipette tip, and deflects the distance adjustment element in accordance with a given program.

Such a program may be a simple formula assigning a particular deflection to each weight force or each liquid level height.

FIG. 5 shows a compensation element 3 to which a removal unit (pipette) is attached, such that pressure acting on the removal tip from below is compensated by an evasive upward movement.

In FIG. 6 a removal unit 2 is shown having a compensation element 3 integrated in a certain area of its wall. This may be realized by adapting a portion of the wall to be elastic using a two-component injection molding method, or by configuring a portion of the wall as a bellows, as shown here.

If the underpressure in the removal unit is constant, or at least uniform, the lower part of the removal unit becomes continuously heavier because of the increasing amount of liquid taken up; the tip may therefore also be lowered automatically, that is, the compensation element acts as a distance adjustment element.

In FIG. 7 a vessel 1 is shown, the bottom of which is made of a foamed material, which is sealed towards the inside to ensure sufficient tightness to liquids. This foamed material must have sufficient elasticity to be able to act as a compensation element 3. Such vessels may be produced by using a two-component injection molding process, for example.

An advantage of such vessels is that they can be inserted in already existing holders for disposable vessels.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A device for taking up liquid from a vessel having a bottom with a curved surface, the device comprising a removal unit having a removal tip formed as a channel surrounded by a wall, the removal tip having at its end an end surface defined by the surrounding wall, wherein the removal tip or the vessel bottom is configured or arranged relative to each other such that an area of the surface of the vessel bottom on which the removal tip would touch down, when the removal tip is inserted into the vessel, and an area of the end surface of the removal tip are tilted relative to each other at least in one portion of the two surface areas, such that the two surface areas are not parallel at the tilted portion, and wherein the removal tip is arranged eccentrically to an apex of curvature of the vessel bottom surface, such that when the removal tip touches down on the vessel bottom there will always result a gap between the at least one portion of the surface area of the vessel bottom and the end surface area of the removal tip, so that the removal tip is prevented from suctioning to the vessel bottom and the liquid flows through the gap into the removal unit.

2. The device according to claim 1, wherein the bottom surface of the vessel is positioned so as to be oblique relative to the end surface of the removal tip.

3. The device according to claim 1, wherein the end surface of the removal tip is beveled relative to a longitudinal axis of the removal tip.

4. The device according to claim 1, wherein the end surface of the removal tip has a shape deviating from a planar surface.

5. The device according to claim 1, further comprising at least one compensation element designed to ensure that, when the removal tip touches the vessel bottom, the vessel or the removal tip will perform an evasive movement in a direction of relative movement between the removal tip and vessel.

6. The device according to claim 5, wherein the compensation element is arranged in a guide unit comprising guide elements that guide the at least one compensation element, a holding device for the vessel, the vessel, or the removal unit along a straight path.

7. The device according to claim 6, wherein the guide unit comprises a sleeve having walls and at least one opening at a top side of the sleeve, and wherein the walls of the sleeve form the guide elements.

8. The device according to claim 7, wherein the sleeve has a length such that it receives the at least one compensation element.

9. The device according to claim 8, wherein the sleeve length is such that it receives the holding device together with the compensation element.

10. The device according to claim 8, wherein the sleeve length is such that it receives the at least one compensation element together with at least part of the vessel or part of the removal unit.

11. The device according to claim 5, wherein the at least one compensation element comprises at least one element selected from the group comprising active and passive elements.

12. The device according to claim 5, wherein the at least one compensation element comprises at least one element selected from the group comprising springs, resilient materials, piezo elements, muscle wires, and motors.

13. The device according to claim 5, wherein the at least one compensation element is configured as a distance adjustment element.

14. The device according to claim 1, further comprising a calibration element to calibrate a distance between the vessel bottom and the end of the removal tip.

15. A method for taking up liquid from a liquid-filled vessel having a curved bottom surface, the method comprising providing a removal unit having a removal tip formed as a channel surrounded by a wall, the removal tip having at its end an end surface defined by the surrounding wall, arranging the removal tip eccentrically to an apex of curvature of the vessel bottom, and tilting an area of the surface of the vessel bottom on which the removal tip would touch down, when the removal tip is inserted into the vessel, and an area of the end surface of the removal tip relative to each other at least in one portion of the two surface areas, such that the two surfaces are not parallel at the tilted portion, such that when the removal tip touches down on the vessel bottom there will always result a gap between the at least one portion of the surface area of the vessel bottom and the end surface of the removal tip, so that the removal tip is prevented from suctioning to the vessel bottom and the liquid flows through the gap into the removal unit.

* * * * *